US012728179B2

(12) United States Patent
Wandera et al.

(10) Patent No.: US 12,728,179 B2
(45) Date of Patent: Sep. 8, 2026

(54) FRAGRANCE-CONTAINING CROSSLINKED GELS

(71) Applicant: AMTEK RESEARCH INTERNATIONAL LLC, Lebanon, OR (US)

(72) Inventors: Daniel Wandera, Corvallis, OR (US); Richard W. Pekala, Corvallis, OR (US); Wyatt Self, Albany, OR (US)

(73) Assignee: AMTEK RESEARCH INTERNATIONAL LLC, Lebanon, OR (US)

( * ) Notice: Subject to any disclaimer, the term of this patent is extended or adjusted under 35 U.S.C. 154(b) by 887 days.

(21) Appl. No.: 18/002,843

(22) PCT Filed: Jun. 29, 2021

(86) PCT No.: PCT/US2021/039660

§ 371 (c)(1),
(2) Date: Dec. 21, 2022

(87) PCT Pub. No.: WO2022/006141

PCT Pub. Date: Jan. 6, 2022

(65) Prior Publication Data

US 2023/0241277 A1 Aug. 3, 2023

Related U.S. Application Data

(60) Provisional application No. 63/047,459, filed on Jul. 2, 2020.

(51) Int. Cl.

| | |
|---|---|
| ***A61L 9/04*** | (2006.01) |
| ***A61L 9/012*** | (2006.01) |
| ***A61L 9/12*** | (2006.01) |

(52) U.S. Cl.
CPC ............... *A61L 9/048* (2013.01); *A61L 9/012* (2013.01); *A61L 9/125* (2013.01)

(58) Field of Classification Search
CPC ........... A61L 9/048; A61L 9/125; A61L 9/012
USPC .......................................................... 512/4, 1
See application file for complete search history.

(56) References Cited

U.S. PATENT DOCUMENTS 8,664,292 B2 3/2014 Pavlin
2005/0267231 A1* 12/2005 Pavlin ..................... C08L 51/02 523/102

FOREIGN PATENT DOCUMENTS

EP 0663212 A2 7/1995
WO 03090718 A1 11/2003

OTHER PUBLICATIONS

International Preliminary Report on Patentability dated Jan. 12, 2023 received in international patent application No. PCT/US2021/039660.
Ahmed, "Hydrogel: Preparation, characterization, and applications: A review", Journal of Advanced Research, vol. 6, Issue 2, 2015, pp. 105-121, ISSN 2090-1232.
International Search Report and Written Opinion dated Nov. 4, 2021 issued in international patent application No. PCT/US2021/039660.
Lorke et al. "Covalent cross-linking of polymers at room temperature", International Journal of Adhesion and Adhesives, vol. 91, 2019, pp. 150-159, ISSN 0143-7496.
Mantha et al. "Smart Hydrogels in Tissue Engineering and Regenerative Medicine" Materials (Basel, Switzerland), vol. 12, Issue 20, Oct. 12, 2019 (Oct. 12, 2019) (33 pages).

* cited by examiner

*Primary Examiner* — Jessica Whiteley
(74) *Attorney, Agent, or Firm* — Dorsey & Whitney LLP

(57) ABSTRACT

Spill-resistant gels with fragrance immobilized within a covalently cross-linked matrix and composites containing the spill-resistant gels are disclosed herein. The covalently cross-linked gel provides low diffusive resistance, but high spill resistance.

14 Claims, 3 Drawing Sheets

FRAGRANCE-CONTAINING CROSSLINKED GELS

CROSS-REFERENCE TO RELATED APPLICATIONS

This patent application is a U.S. National Stage filing under 35 U.S.C. 371 of International Patent Application No. PCT/2021/039660, entitled FRAGRANCE-CONTAINING CROSSLINKED GELS, filed on Jun. 29, 2021, which claims priority to U.S. Provisional Patent Application No. 63/047,459, entitled SPILL-RESISTANT GELS, filed on Jul. 2, 2020, each of which is incorporated herein by reference in its entirety.

COPYRIGHT NOTICE

© 2021 Amtek Research International LLC. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 C.F.R. § 1.71(d).

TECHNICAL FIELD

This disclosure relates to fragrance-containing cross-linked gels, such as for use as air fresheners. The fragrance-loaded gels can have high fragrance content and also be spill-resistant.

BACKGROUND INFORMATION

Air fresheners for personal, home, or automotive use preferably allow for continuous delivery of fragrance compounds without the need for external energy sources. Membrane-based air fresheners were developed in the 1970's. One of the benefits of membrane-based air fresheners is that they tend to not spill, even if dropped. However, the membrane-based air fresheners can suffer from inconsistent perfume release rates. A need exists for alternative air fresheners that will not spill.

SUMMARY OF THE DISCLOSURE

The disclosed spill-resistant gels contain fragrance immobilized within a covalently cross-linked matrix. The fragrance is diffusively releasable from the matrix. Because the covalently cross-linked matrices can be formed at low concentration, they offer low diffusive resistance and a structure that can resist spillage.

DETAILED DESCRIPTION

Figure 1:
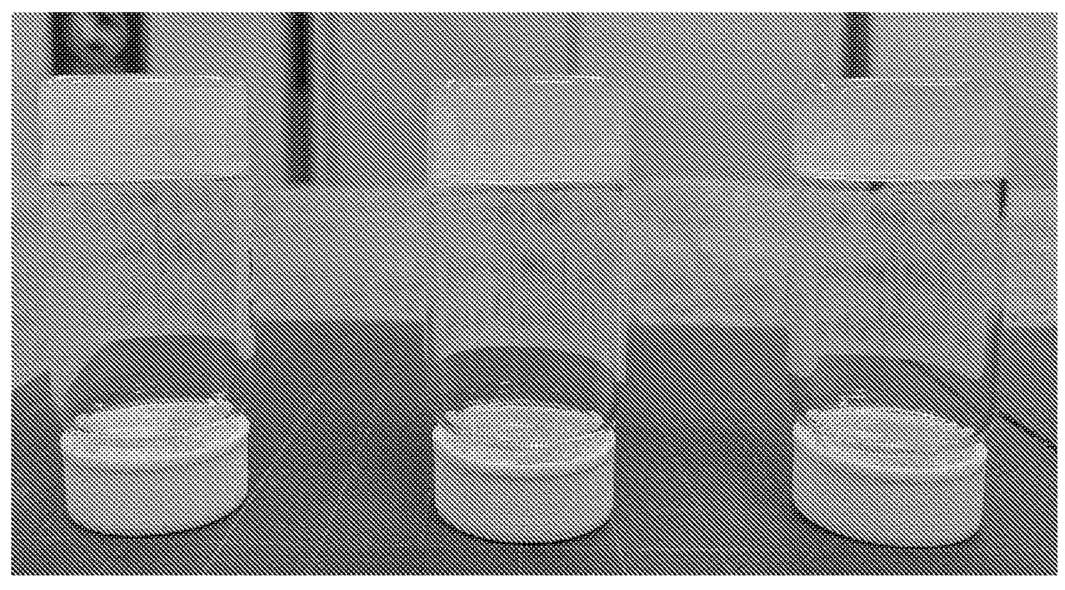
FIG. 1 depicts spill-resistant gels made according to exemplary methods disclosed herein: (a) HEMA polymer gel containing 60% Fresh and Clean fragrance (Example 1, left); (b) HEMA polymer gel containing 80% Fresh and Clean fragrance (Example 2, middle); and (c) and HEMA/DEGDA polymer gel containing 80% Fresh and Clean fragrance (Example 4, right).
Figure 2:
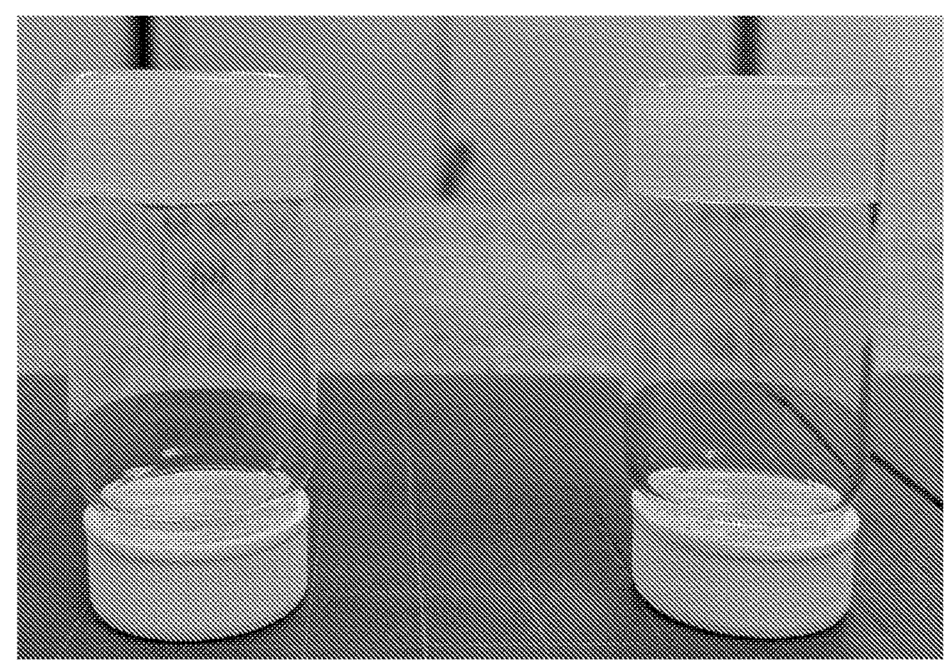
FIG. 2 depicts spill-resistant gels made according to exemplary methods disclosed herein: (a) HEMA polymer gel containing 60% Orange Fruit fragrance (Example 5, left); and (b) HEMA/DEGDA polymer gel containing 60% Orange Fruit fragrance (Example 6, right).
Figure 3:
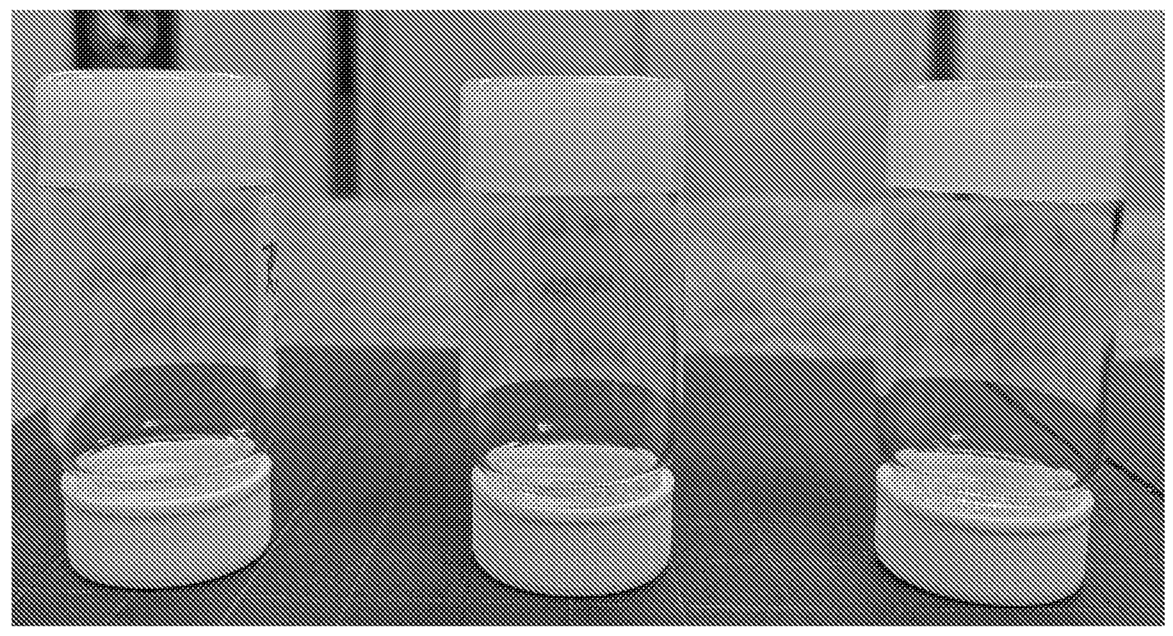
FIG. 3 depicts spill-resistant gels made according to exemplary methods disclosed herein: (a) HEMA polymer gel containing 60% Cherry, Black fragrance (Example 7, left); (b) HEMA/DEGDA polymer gel containing 60% Cherry, Black fragrance (Example 8, middle); and (c) HEMA/DEGDA polymer gel containing 80% Cherry, Black fragrance (Example 9, right).
Figure 4:
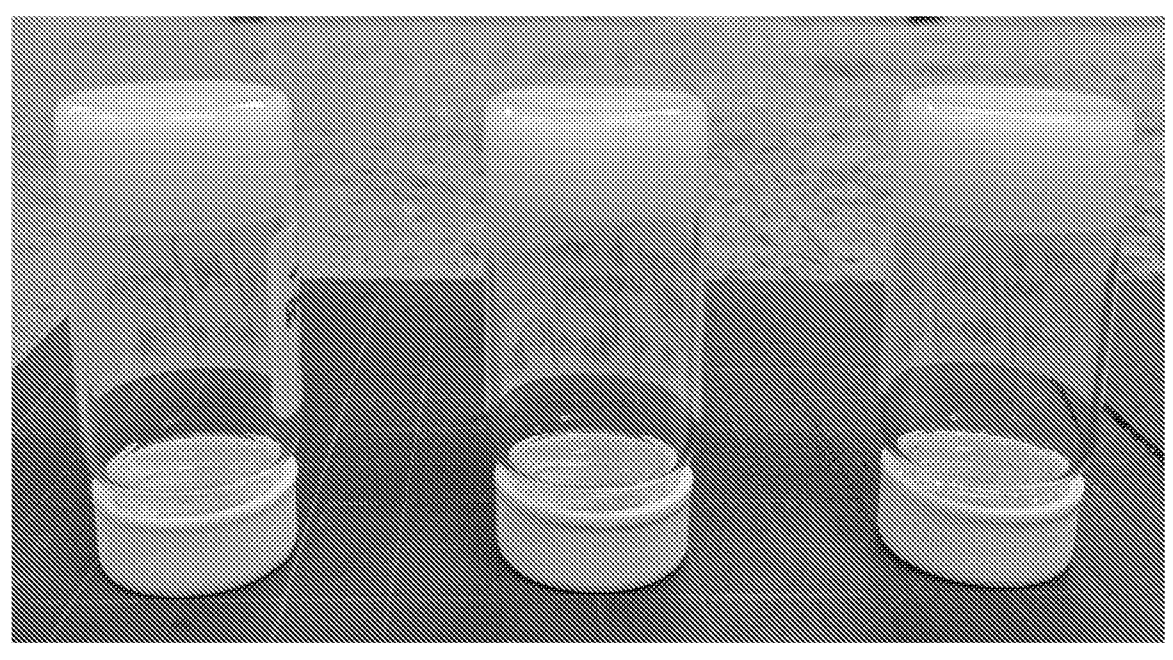
FIG. 4 depicts spill-resistant gels made according to exemplary methods disclosed herein: (a) HEMA polymer gel containing 60% Febreze Air Freshener, Meadows & Rain (Example 10, left); (b) HEMA/DEGDA polymer gel containing 60% Febreze Air Freshener, Meadows & Rain (Example 12, middle); and (c) HEMA polymer gel containing 80% Febreze Air Freshener, Meadows & Rain (Example 11, right).
Figure 5:
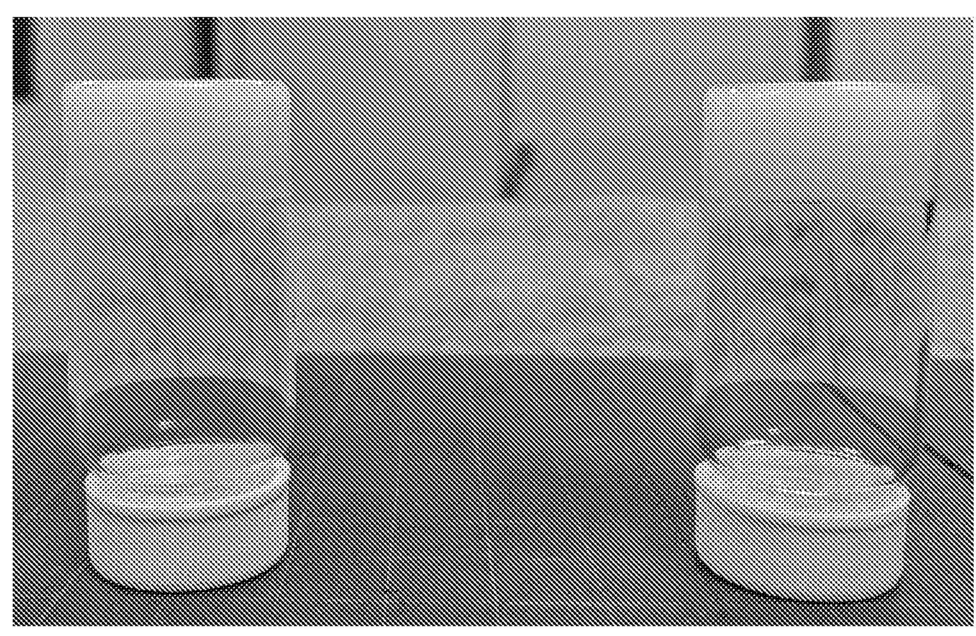
FIG. 5 depicts spill-resistant gels made according to exemplary methods disclosed herein: (a) HEMA polymer gel containing 70% Febreze Air Freshener, Bora Bora Waters (Example 13, left); and (b) HEMA/DEGDA polymer gel containing 70% Febreze Air Freshener, Bora Bora Waters (Example 14, right).
Figure 6:
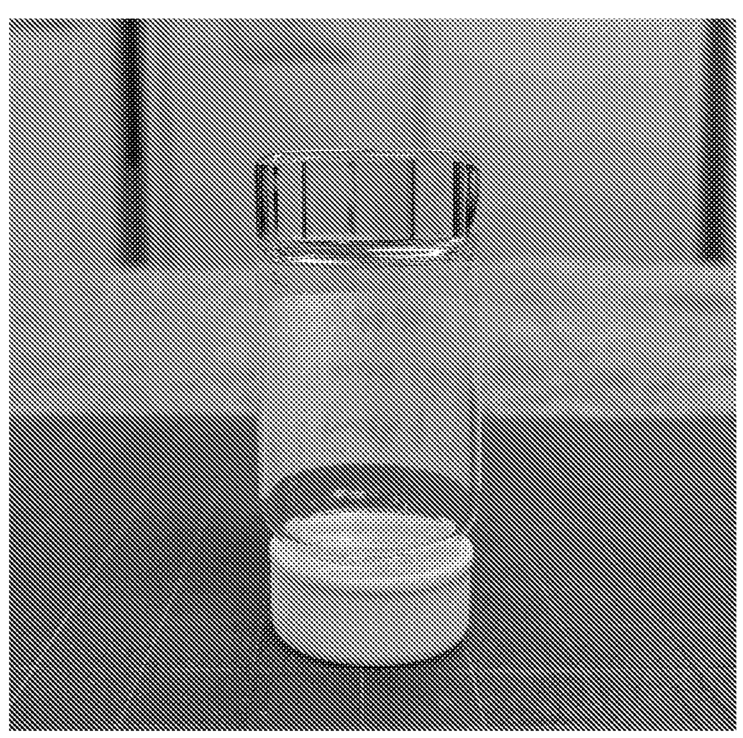
FIG. 6 depicts TMOS sol-gel containing 90% Fresh and Clean fragrance concentrate (Example 15).

The following describes the production of spill-resistant gels containing fragrance immobilized within a covalently cross-linked matrix and in which the fragrance is diffusively releasable from the matrix. The spill-resistant gels can be formed from monomers dissolved in fragrance oil and subsequently covalently cross-linked. The color, appearance, smell, and mechanical properties of the spill-resistant gels can often be enhanced with the addition of other additives, such as a fiber, salt, colloid, soluble or insoluble powder, particulate, soluble polymer not integrated into the matrix, or combination thereof.

The fragrance can contain an essential oil and other natural products. The fragrance constitutes at least 60% by weight of the spill-resistant gel (such as 60% to 95%). Preferably, the fragrance constitutes at least 80% by weight of the spill-resistant gel (such as 80% to 95%). Even more preferably, the fragrance constitutes at least 90% by weight of the spill-resistant gel (such as 90% to 95%). The fragrance can be supplied by a variety of vendors, such as Agilex Fragrances.

The matrix (such as the polymer network or inorganic sol-gel) of the spill-resistant gels can have a low concentration. For example, the mass concentration of the polymer network or inorganic sol-gel in the fragrance can be about 1% to about 40%, about 2% to about 20%, or about 5% to about 10% on a weight-to-weight basis. Segments of the matrix have reacted polymers, monomers, oligomers, cross-linkers, or combinations thereof. For example, segments of the matrix can include acrylamide, methacrylamide, vinylpyrrolidone, acrylate, methacrylate, resorcinol, bis-acrylamide, N,N'-diallyltartramide, glyoxal, formaldehyde, 2-acrylamido-2-methyl-1-propanesulfonic acid, metal alkoxide (such as silica alkoxide, including tetramethyl orthosilicate (TMOS) and tetraethyl orthosilicate (TEOS)), or derivatives of any of the foregoing.

Furthermore, the spill-resistant gels can be part of a composite. The composite can include a substrate (such as a freestanding porous substrate). The spill-resistant gels can be formed at least partially on a surface of the substrate, at least partially within pores of the substrate (if present), or both. Examples of the substrate include a foam, a mat (e.g., a non-woven or woven glass or polymer mat with or without ribs), a sheet, a film, a web, a membrane, or a combination thereof. “Freestanding” refers to a substrate having sufficient mechanical properties to permit manipulation such as winding and unwinding of the substrate for use in an energy storage device assembly process. To the extent the pores of the substrate are not filled with the spill-resistant gel, the pores could potentially be filled with free fragrance (i.e., non-immobilized fragrance).

The spill-resistant gels can be part of an air freshener, such as for personal, home, or automotive use. The spill-resistant gels can be formed into a desired shape with the use of a mold or can be cut or otherwise shaped after gel formation. For example, the spill-resistant gels can have a size and shape compatible with use in the cabin of an automobile. In that example, the air freshener can have a size and shape appealing to user, but also compatible with the rate of evaporation of the fragrance from the air freshener. Or stated another way, the volume of the spill-resistant gel can be selected to evaporatively and diffusively deliver a sufficient quantity of fragrance from the air freshener, based on the release profile of the particular spill-resistant gel.

Methods of forming the spill-resistant gels are also disclosed herein. In one variation, monomer, oligomer, cross-linker, polymer, polymer precursor, or combination thereof, is mixed with a liquid phase containing the fragrance oil. The monomer, oligomer, cross-linker, polymer, polymer precursors, or combination thereof, is then reacted to form a covalently cross-linked matrix that immobilizes the liquid phase, thereby forming the spill-resistant gel.

Additives, substrates, or both may be present during the reaction. For example, additives can be mixed with the liquid phase and the monomer, oligomer, cross-linker, polymer, polymer precursor, or combination thereof, prior to the reaction.

One of skill in the art, with the benefit of this disclosure, should understand that a number of reactions can be used to form the covalently cross-linked matrix. For example, monomers can be reacted with cross-linkers to form the covalently cross-linked matrix, and likewise for oligomers. Some cross-linkers, such as bis-acrylamide, or monomers, such as HEMA, can be reacted by themselves to form the covalently cross-linked polymer network. Alternatively, polymers can be reacted with cross-linkers to form the covalently cross-linked polymer network. Additionally, polymer precursors can be formed and then reacted with cross-linkers to form the covalently cross-linked polymer network.

Non-limiting examples of the monomers, oligomers, and polymer precursors prior to the reacting step are acrylamide, methacrylamide, acrylic acid, acrylate, methacrylate, resorcinol, N-vinylpyrrolidone, and derivatives of any of the foregoing. Non-limiting examples of derivatives include methyl acrylate, ethyl acrylate, 2-carboxyethyl acrylate, methacrylic acid, hydroxymethyl methacrylate, hydroxyethyl methacrylate, hydroxyethoxyethyl methacrylate, hydroxydiethoxyethyl methacrylate, methoxyethyl methacrylate, methoxyethoxyethyl methacrylate, methoxydiethoxyethyl methacrylate, aminoethyl methacrylate, glyceryl methacrylate, propylene glycol methacrylate, N-isopropylacrylamide, N,N-dimethylacrylamide, N-hydroxyethyl acrylamide, N-(isobutoxymethyl)acrylamide, N-(3-methoxypropyl)acrylamide, and N-[tris(hydroxymethyl)methyl]acrylamide.

Non-limiting examples of the polymers prior to the reacting step are linear polyacrylamide, polymethacrylamide, polyacrylate, polymethacrylate, polyvinylpyrrolidone, or derivatives of any of the foregoing, or copolymers of any of the foregoing.

The cross-linker is a multi-functional molecule, such as a tri- or bi-functional molecule. Non-limiting examples of cross-linkers include bis-acrylamide, N,N'-diallyltartramide, ethylene glycol dimethacrlyate, di(ethylene glycol) diacrylate, formaldehyde, and glyoxal. One skilled in the art, with the benefit of this disclosure, should understand that a number of cross-linkers known in the art can be used.

The reaction to form the covalently cross-linked polymer network can be free-radically initiated, such as photochemically or thermally induced. Non-limiting examples of initiators are ammonium persulfate, sodium persulfate, 2,2'-azobis(2-methylpropionitrile), benzoyl peroxide, and dicumyl peroxide. One of skill in the art, with the benefit of this disclosure, should understand that a number of known initiators could be used.

Non-limiting examples of metal alkoxides include including tetramethyl orthosilicate (TMOS) and tetraethyl orthosilicate (TEOS)). The metal alkoxides form a sol-gel. For example, an alcohol (e.g., methanol), deionized water, and ammonia hydroxide ($NH_4OH$)/hydrochloric acid (HCl) can be used as the catalyst system.

Additional advantages of the disclosed spill-resistant gels, or composites containing the spill-resistant gels, will be apparent from the following examples.

EXAMPLES

Example 1

Polymer gel containing 60% Fresh and Clean fragrance was prepared using the following ingredients:

1.91 g of 2-Hydroxyethyl methacrylate (HEMA), 98% (Sigma-Aldrich)

0.09 g of Luperox® A98, Benzoyl peroxide (BP) reagent grade, ≥98% (Sigma-Aldrich)

3 g of Fresh and Clean Fragrance concentrate (Gemlite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 2

Polymer gel containing 80% Fresh and Clean fragrance was prepared using the following ingredients:

0.91 g of 2-Hydroxyethyl methacrylate (HEMA), 98% (Sigma-Aldrich)

0.09 g of Luperox® A98, Benzoyl peroxide (BP) reagent grade, ≥98% (Sigma-Aldrich)

4 g of Fresh and Clean Fragrance concentrate (Gemlite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 3

Polymer gel containing 60% Fresh and Clean fragrance was prepared using the following ingredients:

1.07 g of 2-Hydroxyethyl methacrylate (HEMA), 98% (Sigma-Aldrich)

0.88 g of Di(ethylene glycol) diacrylate (DEGDA) technical grade, 75% (Sigma-Aldrich)

0.05 g of Luperox® A98, Benzoyl peroxide (BP) reagent grade, 98% (Sigma-Aldrich)

3 g of Fresh and Clean Fragrance concentrate (Gemlite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 4

Polymer gel containing 80% Fresh and Clean fragrance was prepared using the following ingredients:

0.52 g of 2-Hydroxyethyl methacrylate (HEMA), 98% (Sigma-Aldrich)

0.43 g of Di(ethylene glycol) diacrylate (DEGDA) technical grade, 75% (Sigma-Aldrich)

0.05 g of Luperox® A98, Benzoyl peroxide (BP) reagent grade, ≥98% (Sigma-Aldrich)

4 g of Fresh and Clean Fragrance concentrate (Gemlite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 5

Polymer gel containing 60% Orange Fruit fragrance was prepared using the following ingredients:

1.91 g of 2-Hydroxyethyl methacrylate (HEMA), 98% (Sigma-Aldrich)

0.09 g of Luperox® A98, Benzoyl peroxide (BP) reagent grade, ≥98% (Sigma-Aldrich)

3 g of Orange Fruit Fragrance concentrate (Gemlite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 6

Polymer gel containing 60% Orange Fruit fragrance was prepared using the following ingredients:

1.07 g of 2-Hydroxyethyl methacrylate (HEMA), 98% (Sigma-Aldrich)

0.88 g of Di(ethylene glycol) diacrylate (DEGDA) technical grade, 75% (Sigma-Aldrich)

0.05 g of Luperox® A98, Benzoyl peroxide (BP) reagent grade, 98% (Sigma-Aldrich)

3 g of Orange Fruit Fragrance concentrate (Gemlite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 7

Polymer gel containing 60% Cherry, Black fragrance was prepared using the following ingredients:

1.91 g of 2-Hydroxyethyl methacrylate (HEMA), 98% (Sigma-Aldrich)

0.09 g of Luperox® A98, Benzoyl peroxide (BP) reagent grade, ≥98% (Sigma-Aldrich)

3 g of Cherry Black Fragrance concentrate (Gem lite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 8

Polymer gel containing 60% Cherry, Black fragrance was prepared using the following ingredients:

1.07 g of 2-Hydroxyethyl methacrylate (HEMA), 98% (Sigma-Aldrich)

0.88 g of Di(ethylene glycol) diacrylate (DEGDA) technical grade, 75% (Sigma-Aldrich)

0.05 g of Luperox® A98, Benzoyl peroxide (BP) reagent grade, ≥98% (Sigma-Aldrich)

3 g of Cherry Black Fragrance concentrate (Gem lite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 9

Polymer gel containing 80% Cherry, Black fragrance was prepared using the following ingredients:

0.52 g of 2-Hydroxyethyl methacrylate (HEMA), 98% (Sigma-Aldrich)

0.43 g of Di(ethylene glycol) diacrylate (DEGDA) technical grade, 75% (Sigma-Aldrich)

0.05 g of Luperox® A98, Benzoyl peroxide (BP) reagent grade, ≥98% (Sigma-Aldrich)

4 g of Cherry Black Fragrance concentrate (Gem lite Soap & Candle Supply)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid gel with no free liquid was formed.

Example 10

Polymer gel containing 60% Febreze Air Freshener, Meadows & Rain was prepared using the following ingredients:

1.96 g of 2-Hydroxyethyl methacrylate (HEMA), 98% (Sigma-Aldrich)

0.04 g of Luperox® A98, Benzoyl peroxide (BP) reagent grade, ≥98% (Sigma-Aldrich)

3 g of Febreze Air Freshener, Meadows & Rain (Procter & Gamble)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid white gel with no free liquid was formed.

Example 11

Polymer gel containing 80% Febreze Air Freshener, Meadows & Rain was prepared using the following ingredients:

0.98 g of 2-Hydroxyethyl methacrylate (HEMA), 98% (Sigma-Aldrich)

0.02 g of Luperox® A98, Benzoyl peroxide (BP) reagent grade, ≥98% (Sigma-Aldrich)

4 g of Febreeze Air Freshener, Meadows & Rain (Procter & Gamble)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid white gel with no free liquid was formed.

Example 12

Polymer gel containing 60% Febreze Air Freshener, Meadows & Rain was prepared using the following ingredients:

1.09 g of 2-Hydroxyethyl methacrylate (HEMA), 98% (Sigma-Aldrich)

0.89 g of Di(ethylene glycol) diacrylate (DEGDA) technical grade, 75% (Sigma-Aldrich)

0.02 g of Luperox® A98, Benzoyl peroxide (BP) reagent grade, ≥98% (Sigma-Aldrich)

3 g of Febreze Air Freshener, Meadows & Rain (Procter & Gamble)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid white gel with no free liquid was formed.

Example 13

Polymer gel containing 70% Febreze Air Freshener, Bora Bora Waters was prepared using the following ingredients:

1.47 g of 2-Hydroxyethyl methacrylate (HEMA), 98% (Sigma-Aldrich)

0.03 g of Luperox® A98, Benzoyl peroxide (BP) reagent grade, ≥98% (Sigma-Aldrich)

3.5 g of Febreze Air Freshener, Bora Bora Waters (Procter & Gamble)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid white gel with no free liquid was formed.

Example 14

Polymer gel containing 70% Febreze Air Freshener, Bora Bora Waters was prepared using the following ingredients:

0.81 g of 2-Hydroxyethyl methacrylate (HEMA), 98% (Sigma-Aldrich)

0.67 g of Di(ethylene glycol) diacrylate (DEGDA) technical grade, 75% (Sigma-Aldrich)

0.02 g of Luperox® A98, Benzoyl peroxide (BP) reagent grade, ≥98% (Sigma-Aldrich)

3.5 g of Febreze Air Freshener, Bora Bora Waters (Procter & Gamble)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid white gel with no free liquid was formed.

Example 15

Polymer gel containing 60% Febreze Air Freshener, Blood Orange & Spritz was prepared using the following ingredients:

1.09 g of 2-Hydroxyethyl methacrylate (HEMA), 98% (Sigma-Aldrich)

0.89 g of Di(ethylene glycol) diacrylate (DEGDA) technical grade, 75% (Sigma-Aldrich)

0.02 g of Luperox® A98, Benzoyl peroxide (BP) reagent grade, ≥98% (Sigma-Aldrich)

3 g of Febreze Air Freshener, Blood Orange & Spritz (Procter & Gamble)

The ingredients were weighed into a 20 mL borosilicate glass scintillation vial (Fisher Scientific) and the vial was end capped. The contents were thoroughly mixed using a stir bar on a stir plate at room temperature until all the contents had fully dissolved into the fragrance oil. The solution in the vial was placed in a convention oven for 1 hour to form the gel at 80° C. A firm, solid white gel with no free liquid was formed.

Example 16

Sol-gel containing 90% Fresh and Clean fragrance was prepared using the following ingredients:

0.28 g of Tetramethyl orthosilicate (TMOS), 98% (Sigma-Aldrich)

0.11 g of deionized water that had hydrochloric acid (HCl) added (acidic water)

0.11 g of deionized water that had ammonia hydroxide (NaOH) added (basic water)

4.5 g of Fresh and Clean Fragrance concentrate (Gem lite Soap & Candle Supply) diluted to 30% with CARBOWAX™ Polyethylene Glycol (PEG) 200 (Dow Chemical)

A bulk solution of TMOS was prepared by adding 5.1 g of TMOS to 1.5 g of methanol. A stock solution of the acidic water was prepared by adding 0.1 g of HCl and 1.5 g of methanol to 1 g of deionized water. A stock solution of the basic water was prepared by adding 0.1 g of NaOH and 1.5 g of methanol to 1 g of deionized water. To prepare the sol-gel, the required quantity of diluted fragrance was weighed into a 20 mL borosilicate glass scintillation vial. The required amount of the TMOS solution was then added to the fragrance with constant stirring, followed by the required amount of acidic water and finally the required amount of basic water was added. The final solution was stirred for an extra 2 minutes and left to stand overnight for the sol-gel to form. A clear, transparent solid gel was formed.

Example 17

Sol-gel containing 90% Fresh Linen fragrance was prepared using the following ingredients:

0.28 g of Tetramethyl orthosilicate (TMOS), 98% (Sigma-Aldrich);

0.11 g of deionized water that had hydrochloric acid (HCl) added (acidic water);

0.11 g of deionized water that had ammonia hydroxide (NaOH) added (basic water); and 4.5 g of Fresh Linen Fragrance concentrate (Gem lite Soap & Candle Supply) diluted to 30% with CARBOWAX™ Polyethylene Glycol (PEG) 200 (Dow Chemical).

A bulk solution of TMOS was prepared by adding 5.1 g of TMOS to 1.5 g of methanol. A stock solution of the acidic water was prepared by adding 0.1 g of HCl and 1.5 g of methanol to 1 g of deionized water. A stock solution of the basic water was prepared by adding 0.1 g of NaOH and 1.5 g of methanol to 1 g of deionized water. To prepare the sol-gel, the required quantity of diluted fragrance was weighed into a 20 mL borosilicate glass scintillation vial. The required amount of the TMOS solution was then added to the fragrance with constant stirring, followed by the required amount of acidic water and finally the required amount of basic water was added. The final solution was stirred for an extra 2 minutes and left to stand overnight for the sol-gel to form. A clear, transparent solid gel was formed.

It will be apparent to those having skill in the art that many changes may be made to the details of the above-described embodiments without departing from the underlying principles of the invention.

The invention claimed is:

1. A spill-resistant gel comprising:

from 60 to 95 wt % of a fragrance; and a covalently cross-linked matrix comprising a polymer network, the polymer network comprising hydroxyethyl methacrylate;

wherein the fragrance is immobilized within the covalently cross-linked matrix and diffusively releasable from the matrix.

2. The spill-resistant gel of claim 1, in which the fragrance comprises an essential oil.

3. The spill-resistant gel of claim 1, in which the fragrance comprises at least 80% to 95% by weight of the spill-resistant gel.

4. The spill-resistant gel of claim 1, wherein a mass concentration of the matrix is about 1% to about 40%, about 2% to about 20%, or about 5% to about 10% on a weight-to-weight basis.

5. The spill-resistant gel of claim 1, wherein the gel further comprises an additive.

6. The spill-resistant gel of claim 5, wherein the additive comprises a fiber, salt, colloid, soluble or insoluble powder, particulate, soluble polymer not integrated into the matrix, or combination thereof.

7. A composite, comprising:

a spill-resistant gel comprising:

from 60 to 95 wt % of a fragrance; and a covalently cross-linked matrix comprising a polymer network, the polymer network comprising hydroxyethyl methacrylate;

wherein the fragrance is immobilized within the covalently cross-linked matrix and diffusively releasable from the matrix; and a freestanding porous substrate with the spill-resistant gel formed at least partially on a surface of the substrate, at least partially within pores of the substrate, or both.

8. The composite of claim 7, wherein the substrate comprises a foam, a mat, a sheet, a film, a web, a membrane, or combination thereof.

9. The composite of claim 7, wherein the substrate comprises a polymer film, a glass mat, or combinations thereof.

10. The composite of claim 7, further comprising free fragrance in at least some of the pores of the substrate not filled with the spill-resistant gel.

11. An air freshener comprising the spill-resistant gel of claim 1.

12. The air freshener of claim 11, in which the air freshener has a size and shape compatible with use in a cabin of an automobile.

13. A method of forming a spill-resistant gel, the method comprising:

mixing hydroxyethyl methacrylate monomers with a liquid phase comprising a fragrance; and reacting the monomers to form a covalently cross-linked matrix that immobilizes the liquid phase, thereby forming the spill-resistant gel.

14. The method of claim 13, further comprising reacting the monomers, in the presence of a freestanding porous substrate, whereby the spill-resistant gel is formed at least partially on a surface of the substrate, at least partially within pores of the substrate, or both.

* * * * *